(12) United States Patent
Inaba et al.

(10) Patent No.: US 7,054,004 B2
(45) Date of Patent: May 30, 2006

(54) CAPILLARY ARRAY AND CAPILLARY ARRAY PHOTODETECTOR

(75) Inventors: Ryoji Inaba, Hitachinaka (JP); Toshiaki Kita, Hitachinaka (JP); Miho Ozawa, Abiko (JP); Tomonari Morioka, Hitachinaka (JP); Akihiro Suzuki, Hitachinaka (JP); Yasushi Shimizu, Hitachinaka (JP); Masaya Kojima, Mito (JP)

(73) Assignee: Hitachi, Ltd., Tokyo (JP)

( * ) Notice: Subject to any disclaimer, the term of this patent is extended or adjusted under 35 U.S.C. 154(b) by 169 days.

(21) Appl. No.: 10/704,827

(22) Filed: Nov. 12, 2003

(65) Prior Publication Data

US 2004/0119011 A1 Jun. 24, 2004

Related U.S. Application Data

(63) Continuation of application No. 10/098,330, filed on Mar. 18, 2002, now abandoned.

(30) Foreign Application Priority Data

Apr. 2, 2001 (JP) ............................. 2001-103206

(51) Int. Cl.
*G01N 21/00* (2006.01)
*C02F 1/40* (2006.01)
(52) U.S. Cl. ....................................... 356/344; 204/603
(58) Field of Classification Search ................ 356/344; 204/601–605
See application file for complete search history.

(56) References Cited

U.S. PATENT DOCUMENTS

| 5,312,535 | A | 5/1994 | Waska et al. | |
|---|---|---|---|---|
| 5,582,705 | A | 12/1996 | Yeung et al. | |
| 5,667,656 | A | 9/1997 | Kambara | |
| 5,790,727 | A | 8/1998 | Dhadwal et al. | |
| 5,833,827 | A | 11/1998 | Anazawa et al. | |
| 5,900,934 | A | 5/1999 | Gilby et al. | |
| 5,938,908 | A | 8/1999 | Anazawa et al. | |
| 6,387,236 | B1 | 5/2002 | Nordman et al. | |
| 6,404,495 | B1 | 6/2002 | Melman et al. | |
| 6,461,492 | B1 * | 10/2002 | Hayashizaki et al. | 204/603 |
| 6,531,041 | B1 * | 3/2003 | Cong et al. | 204/452 |
| 6,805,784 | B1 * | 10/2004 | Kasai et al. | 204/601 |
| 2001/0040095 | A1 * | 11/2001 | Shimizu et al. | 204/603 |
| 2001/0047942 | A1 * | 12/2001 | Kasai et al. | 204/601 |
| 2002/0117398 | A1 * | 8/2002 | Hayashizaki et al. | 204/603 |
| 2003/0155245 | A1 * | 8/2003 | Morioka et al. | 204/601 |
| 2005/0003211 | A1 * | 1/2005 | Harada et al. | 428/435 |

FOREIGN PATENT DOCUMENTS

| JP | 9-80021 | | 3/1997 |
|---|---|---|---|
| JP | 2000-147497 | * | 5/2000 |
| JP | 2001-264293 | * | 9/2001 |

* cited by examiner

*Primary Examiner*—Michael P. Stafira
(74) *Attorney, Agent, or Firm*—Dickstein Shapiro Morin & Oshinsky LLP

(57) ABSTRACT

A multi-focus capillary array that can reduce crosstalk and a capillary array photodetector are provided. On a substrate 20 on which a plurality of capillaries are aligned, a perforation 72 is formed in at least a part of an area in the rear of the capillaries when the capillary array is viewed from the photodetector.

26 Claims, 14 Drawing Sheets

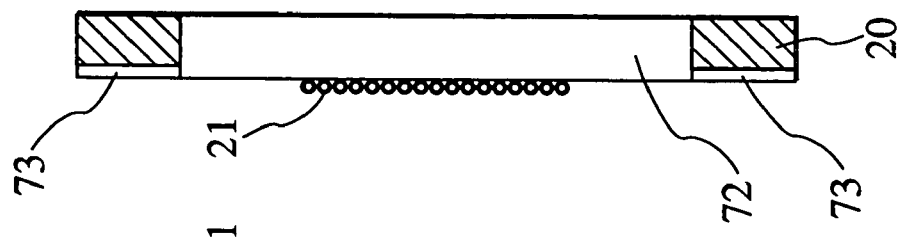
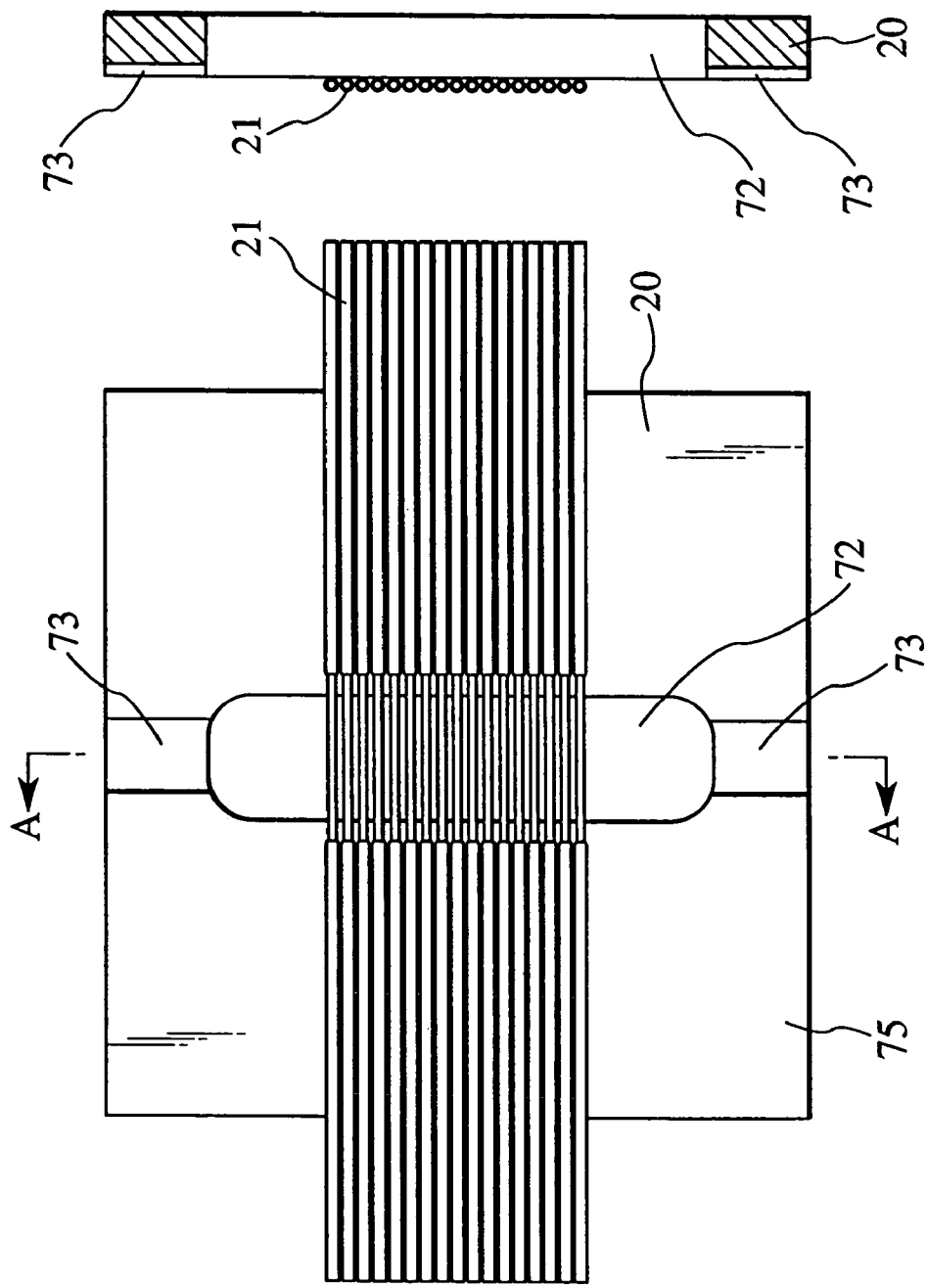

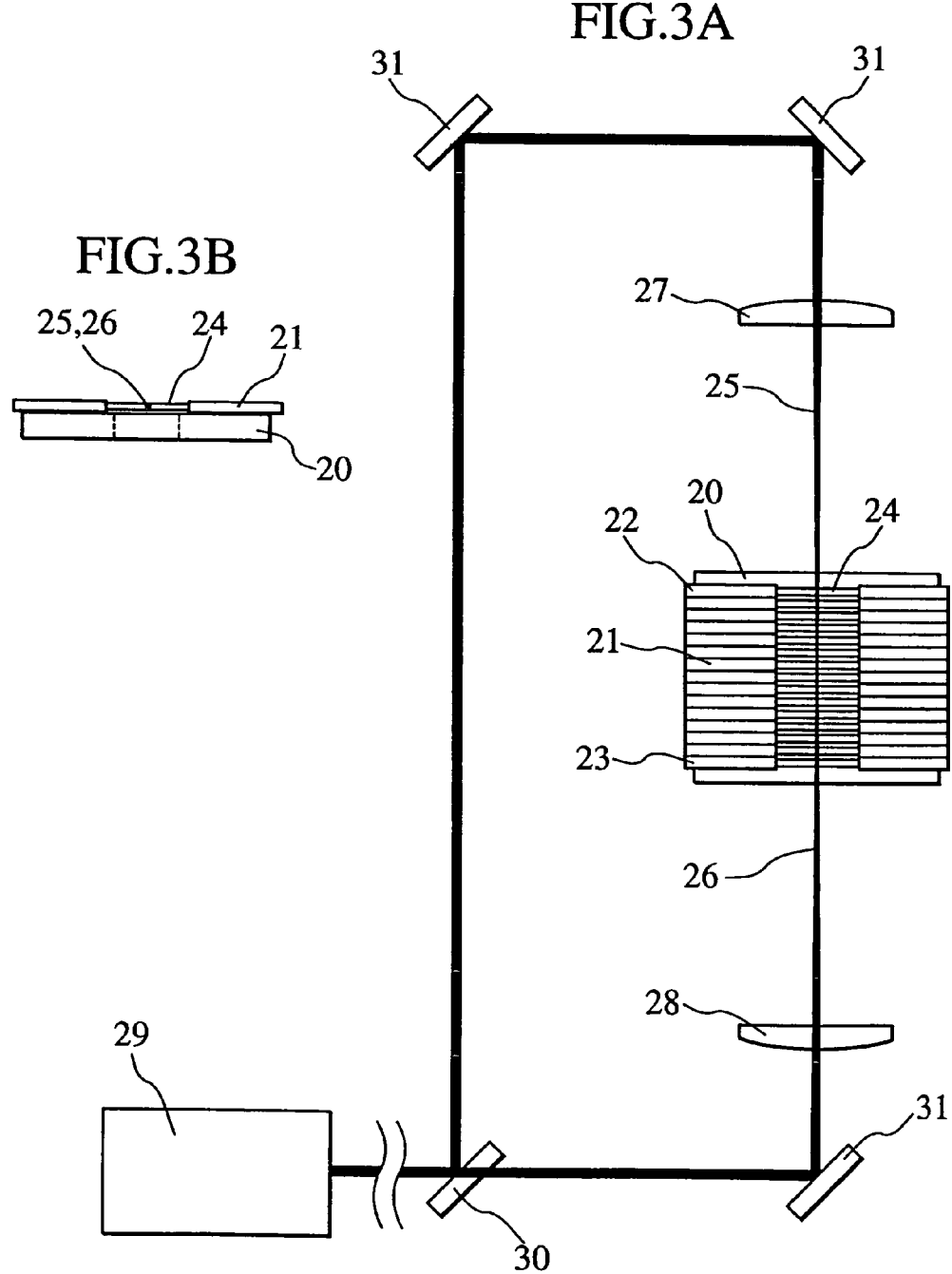

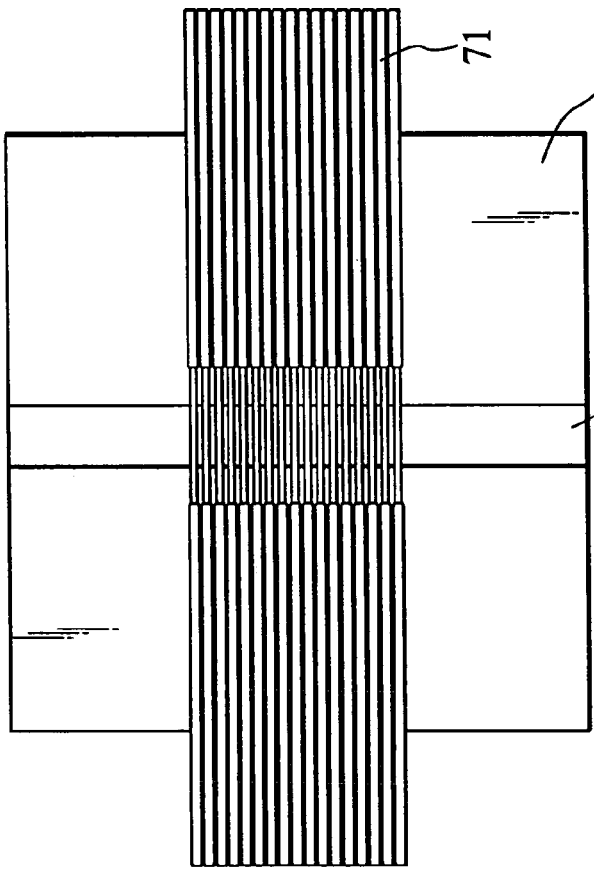
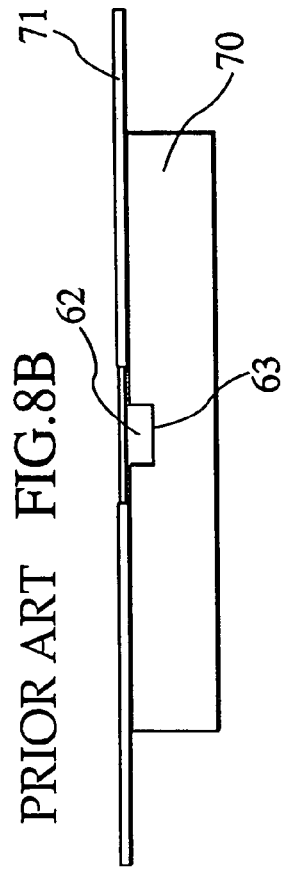
PRIOR ART FIG.8A
PRIOR ART FIG.8B
PRIOR ART FIG.8C

FLUORESCENCE DETECTION SYSTEM

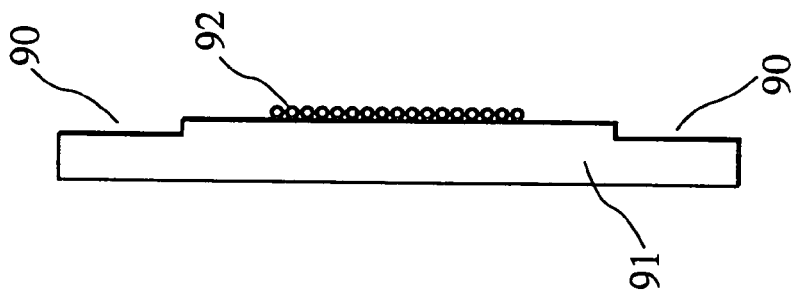
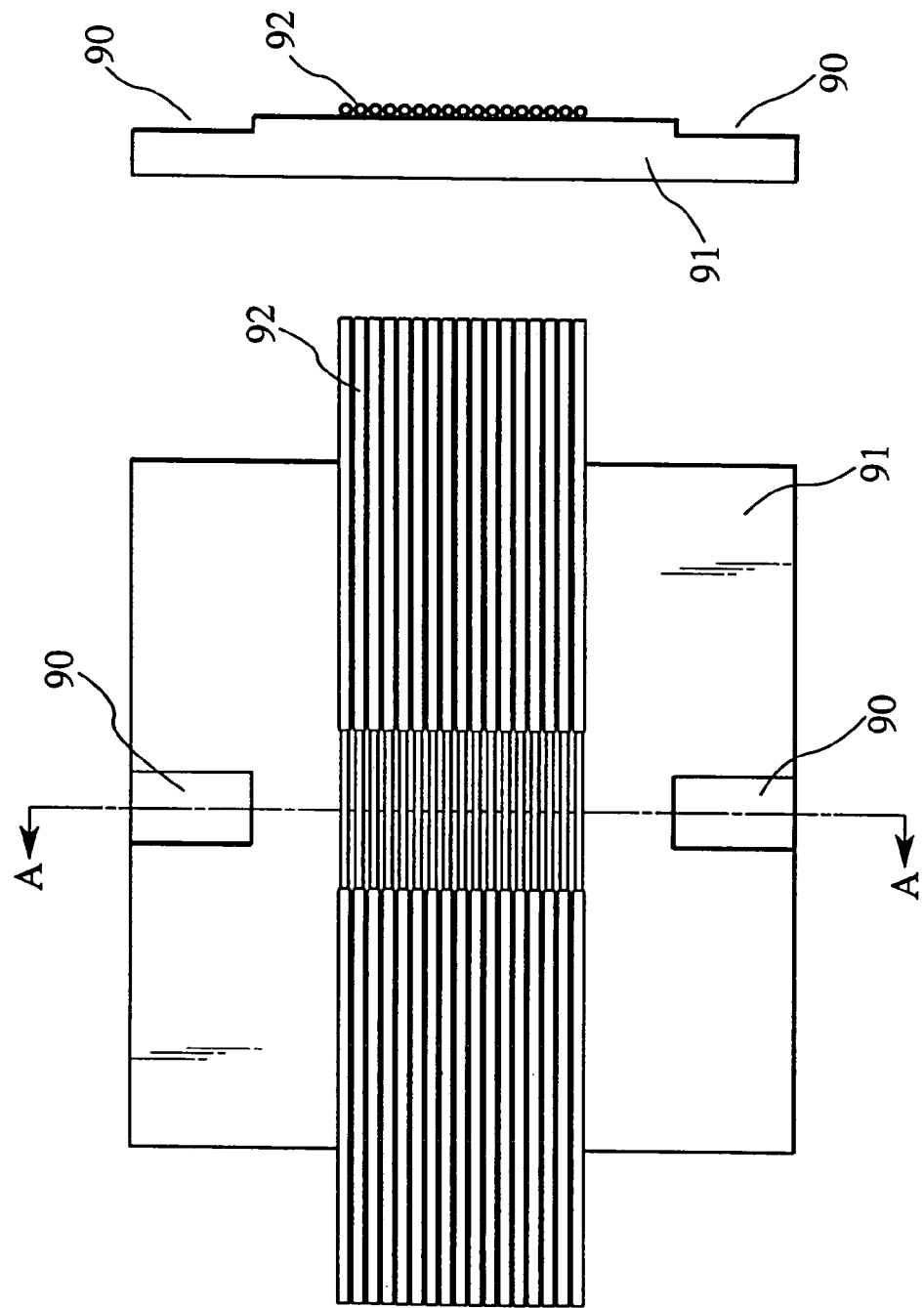

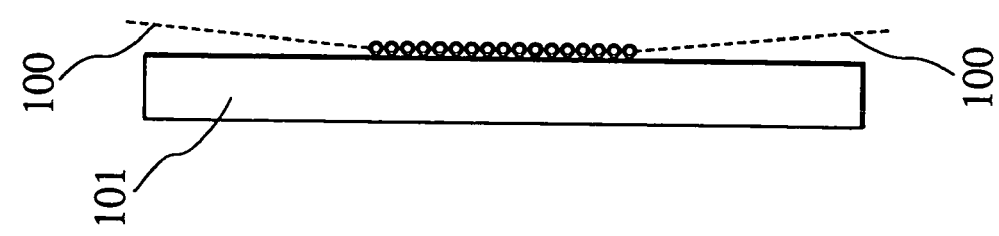
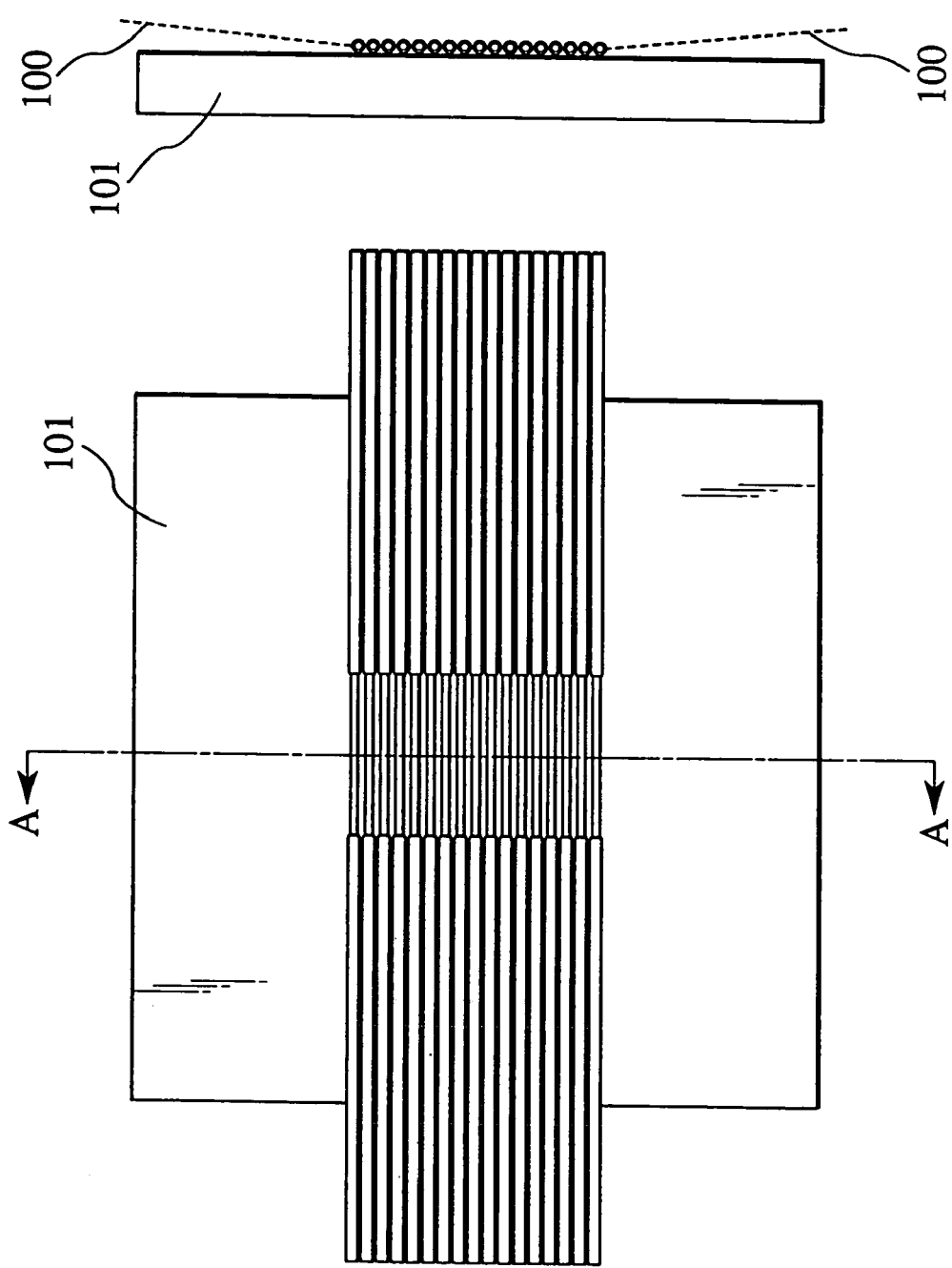

CAPILLARY ARRAY AND CAPILLARY ARRAY PHOTODETECTOR

CROSS-REFERENCE TO RELATED APPLICATION

The present application is a continuation application of U.S. patent application Ser. No. 10/098,330, filed on Mar. 18, 2002 now abandoned, the disclosure of which is incorporated by reference herein.

BACKGROUND OF THE INVENTION

The present invention relates to a capillary array electrophoresis device for separating a sample such as fluorescence labeled DNA and detecting, identifying and analyzing a base sequence, a base length and so on of the sample according to electrophoresis in a capillary, and more particularly, to a capillary array to be incorporated into the capillary array electrophoresis device and a capillary array photodetector for detecting emission from the sample migrating through the capillary array.

Capillary electrophoresis has been utilized for determination of DNA base sequences and DNA base lengths. In the capillary electrophoresis, a sample containing DNA as a measuring object is injected into a capillary made of glass or the like and filled with a polyacrylamide gel or the like, and then a voltage is applied to each of the ends of the capillary. The synthetic DNA in the sample migrates through the capillary to be separated into fragments according to molecular weights thereof and so on, and then a DNA band is generated in the capillary. A fluorescent dye molecule is bonded to each of the synthetic DNA fragments, and emission measuring means measures emission from each of the fragments by way of laser beam irradiation, to thereby determine base sequences, base lengths and the like of the synthetic DNA fragments from the measured fluorescent spectra.

U.S. Pat. No. 5,582,705 discloses a multi-focus system, which is a variation of a system of irradiating a plurality of capillaries with light. In the system, laser beam is irradiated on a capillary at one end or capillaries on both ends of a capillary array comprising a plurality of capillaries aligned in parallel to each other on a planar substrate, and the laser beam is propagated to adjacent capillary or capillaries one by one to ultimately travel across the capillary array so that a photodetector detects emissions generated in the capillary array. Each of the capillaries is applied with a polymer coating, but the polymer coating is not applied at part of the capillaries to be irradiated with a laser beam.

There have been proposed irradiation systems other than the multi-focus system, such as a scanning system wherein a plurality of capillaries to scan each of the capillaries is irradiated with a laser beam (Nature, 359 (1992)), a multi-beam system wherein each of a plurality of capillaries is irradiated with a laser beam (Analytical Chemistry, 65, 956 (1993)), and a batch irradiation system (Analytical Chemistry, 66, 1424 (1004)) wherein a plurality of capillaries are subjected to a batch irradiation with a laser beam that is spread by a cylindrical lens in a direction along which the capillaries are aligned. The multi-focus system has the advantage of excellent detection sensitivity for DNAs as compared with the above systems.

SUMMARY OF THE INVENTION

In the multi-focus system, it is necessary to suppress a relative misalignment among a plurality of capillaries as small as possible in order to propagate a laser beam through the capillaries. Therefore, an alignment precision required for the system is typically realized by fixing the capillaries on a planar glass substrate by so pressing them that the adjacent capillaries contact with one another. Since the laser beam passes through the capillaries thus brought into contact with one another, emissions of and from the laser beam and capillaries are reflected and scattered complicatedly on a surface of each of the capillaries. Further, the scattered light becomes more complicated due to the planar substrate on which the capillaries are aligned.

There is a problem of "crosstalk" in a multi-focus system that a part of emissions from a certain capillary overlaps with a location of emissions of an adjacent capillary due to the scattered light, i.e., signals of the certain capillary are detected as signals of the adjacent capillary.

In view of the problem in the art, an object of the present invention is to provide a multi-focus type capillary array and a capillary array photodetector that allow reduction of the crosstalk.

In order to achieve the object, the present invention provides a capillary array comprising a substrate having a planar capillary holding surface and a plurality of capillaries aligned on the capillary holding surface of the substrate, wherein a laser beam irradiated on a capillary at one end or capillaries at both ends of the plurality of capillaries in a substantially parallel direction with respect to the capillary holding surface propagates to all the plurality of capillaries one by one to travel through the capillaries, and emissions from each of the capillaries are detected in a substantially perpendicular direction with respect to the capillary holding surface, wherein the substrate is provided with a perforation piercing from the capillary holding surface to a back side of the substrate in an area opposing to portions of the plurality of capillaries each of which receives the laser beam irradiation.

It is preferable to secure a possibly largest space free from such an object that can cause the emissions from the capillaries to reflect to reach the photodetector on the rear side of each of the capillaries when the capillary array is viewed from a photodetector for detecting the emissions from the capillaries. Since the substrate is provided with the perforation, the emissions from the capillaries are no longer reflected from the substrate and does not enter the photodetector, thereby reducing the crosstalk.

In conventional irradiation systems other than the multi-focus system, there has been proposed a variation wherein a wide area is secured on the rear side of capillaries when a capillary array is viewed from a photodetector. For example, "Mega BACE", a capillary electrophoresis device manufactured by Molecular Dynamics, Inc. is provided with such area. However, since the device does not employ the multi-focus irradiation, the device does not require such a high level of relative alignment precision as that required in the multi-focus system. The present invention is distinguished from the above-mentioned systems in the ability to reduce the crosstalk while suppressing relative misalignment among the capillaries to a remarkably low level.

Further, in order to achieve the above object, the present invention provides a capillary array comprising a substrate having a planar capillary holding surface and a plurality of capillaries aligned on the capillary holding surface of the substrate, wherein a laser b am irradiated on a capillary at one end or capillaries at both ends of the plurality of capillaries in a substantially parallel direction with respect to the capillary holding surface propagates to all the plurality of capillaries one by one to travel through the capillaries, and emissions from each of the capillaries are detected in a substantially perpendicular direction with respect to the capillary holding surface, wherein the capillary holding surface of the substrate opposing to portions of the plurality of capillaries each of which receives the laser beam irradiation is subjected to a light-scattering prevention treatment or a light-reflection prevention treatment.

Here, the light-scattering prevention treatment or the light reflection prevention treatment may be a monolayer or a multilayer anti-reflection coating. Conventionally, a groove is formed on a planar substrate along a laser light path in order to avoid contact of the laser beam with the planar substrate on which capillary array is formed and, therefore, the glass surface is frosted as it is a frosted glass as a result of the grooving. Elimination of such groove in the rear area of the capillaries when the capillary array is viewed from the photodetector contributes to prevention of the light scattering. That is to say, the light-scattering prevention treatment includes forming a simply flat surface in place of the frosted glass-like surface. A groove for avoiding contact of laser beam with the substrate may be formed only on each of ends of the glass substrate so that the groove is not necessary in the rear area of the capillaries when the capillary array is viewed from the photodetector. Further, it is possible to avoid contact of the laser beam with the planar substrate by downsizing the planar substrate or shifting an irradiation angle of the laser beam parallelly with respect to the planar substrate without forming the groove on the planar substrate.

Further, in order to achieve the above object, the present invention provides a capillary array comprising a substrate having a planar capillary holding surface, a plurality of capillaries aligned on the capillary holding surface of the substrate, scattered light shielding means placed on the plurality of capillaries for shielding areas at which adjacent capillaries contact with each other with a partial area including a central axis of each of the capillaries being not shielded, wherein a laser beam irradiated on a capillary at one end or capillaries at both ends of the plurality of capillaries in a substantially parallel direction with respect to the capillary holding surface propagates to all the plurality of capillaries one by one to travel through the capillaries, and emissions from each of the capillaries are detected through the space between the shielding areas in a substantially perpendicular direction with respect to the capillary holding surface, wherein each of the capillaries is provided with a coating, but is not provided with the coating in an area for receiving the laser beam irradiation thereon, and the scattered light shielding means contacts with the area of the capillaries for which the coating is not provided.

In order to bring the shielding means into direct contact with the coating-removed area of the capillary, a shape of a contact portion of the shielding means with the capillary may be so formed as to mate the capillary having a step-like shape that is formed when the coating is partially removed, or a width of the coating-removed portion of the capillary may be made wider than that of the scattered light shielding means.

In order to achieve the above object, the present invention provides a capillary array photodetector comprising a reference surface with which contacts with a capillary holding surface of a capillary array holding substrate that holds a capillary array, fixing means for fixing the capillary array holding substrate brought into contact with the reference surface by pressing the capillary array holding substrate from the rear surface thereof, a laser light source, an irradiation optical system for setting a part of a light path extending from the light source to be substantially parallel to the capillary holding surface of the capillary array holding substrate contacting with the reference surface, and a photodetector system for detecting emissions, the capillary array photodetector detecting emissions from each of the capillaries, which emissions being caused by laser beam that is irradiated from the irradiation optical system on a capillary at one end or capillaries at both ends of the plurality of capillaries aligned on the capillary holding surface of the capillary array holding substrate fixed on the reference surface with being brought into contact therewith and that propagates to all the plurality of capillaries one by one to travel through the capillaries, wherein the fixing means is provided with a recessed portion opening on a side of the reference surface.

Since it is possible to secure a yet wider space in the rear of the capillaries by attaching the capillary array of the present invention wherein the substrate is provided with the perforation to the capillary array photodetector for detection, opportunities for light that will be reflected from the capillaries to enter the photodetector are reduced, thereby further improving the effect of reducing the crosstalk. In addition, in the case where a capillary array holding means for improving handling of the capillary array is provided in the rear of the capillaries when the capillary array is viewed from the photodetector, the capillary array holding means is also provided with a perforation in order to secure the space as wide as possible in the rear of the capillaries when the capillary array is viewed from the photodetector.

It is preferable to subject a wall that is a background of the capillaries when the capillary array is viewed from the photodetector, such as a surface of the recess on the fixing portion, to the light-scattering prevention treatment or the light reflection prevention treatment. These treatments may be, but not limited to, a non-fluorescent black coating, blackening treatment of a copper surface or patching of a light absorption material.

According to the invention, it is possible to largely reduce the crosstalk otherwise detected from a capillary adjacent to a capillary on which the laser beam is irradiated. In the case where a detection limit of DNA sample is determined on the crosstalk from the adjacent capillaries, the present invention can improve the detection limit and increase the dynamic range.

BRIEF DESCRIPTION OF THE DRAWINGS

FIG. 2A and FIG. 2B each is a schematic view of an example of a capillary array according the present invention; FIG. 2A is a front view of a part of the capillary array fixed on a planar glass substrate, and FIG. 2B is a sectional view taken along the line A—A of FIG. 2A;

FIG. 3A and FIG. 3B are block diagrams respectively showing a detection unit of the capillary array and a guiding path of a laser beam; FIG. 3A is a schematic front view of an example of an optical system of a capillary array photodetector according to the present invention, and FIG. 3B is a top view showing an example of a detection unit of the capillary array;

FIG. 8A, FIG. 8B and FIG. 8C each shows a state wherein a capillary array is mounted on a glass substrate according to a conventional system; FIG. 8A is a front view, FIG. 8B is a side view taken along the line A—A of FIG. 8A, and FIG. 8C is a sectional view viewed from a direction parallel to a light path of a laser beam;

FIG. 12A and FIG. 12B each is a schematic view of another example of a capillary array according to the present invention; FIG. 12A is a front view of a part of the capillary array fixed on a planar glass substrate, and FIG. 12B is a sectional view taken along the line A—A of FIG. 12A;

FIG. 13A and FIG. 13B each is a schematic view of another example of a capillary array according to the present invention; FIG. 13A is a front view of a part of the capillary array fixed on a planar glass substrate, and FIG. 13B is a sectional view taken along the line A—A of FIG. 13A;

FIG. 14A is a front view of the capillary array with a mask, FIG. 14B is a sectional view taken along the line A—A of a conventional capillary array with a mask, FIG. 14C is a sectional view taken along the line A—A of an example of a capillary array according to the present invention, and FIG. 14D is a sectional view taken along the line B—B of the capillary array according to the present invention; FIG. 15A is a front view thereof, and FIG. 15B is a sectional view taken along the line A—A of FIG. 15A.

DETAILED DESCRIPTION OF THE PREFERRED EMBODIMENTS

Embodiments of the present inventions will hereinafter be described with reference to the attached drawings. Electrophoresis using samples each containing DNA will be described below by way of examples.

First Embodiment

Figure 1:
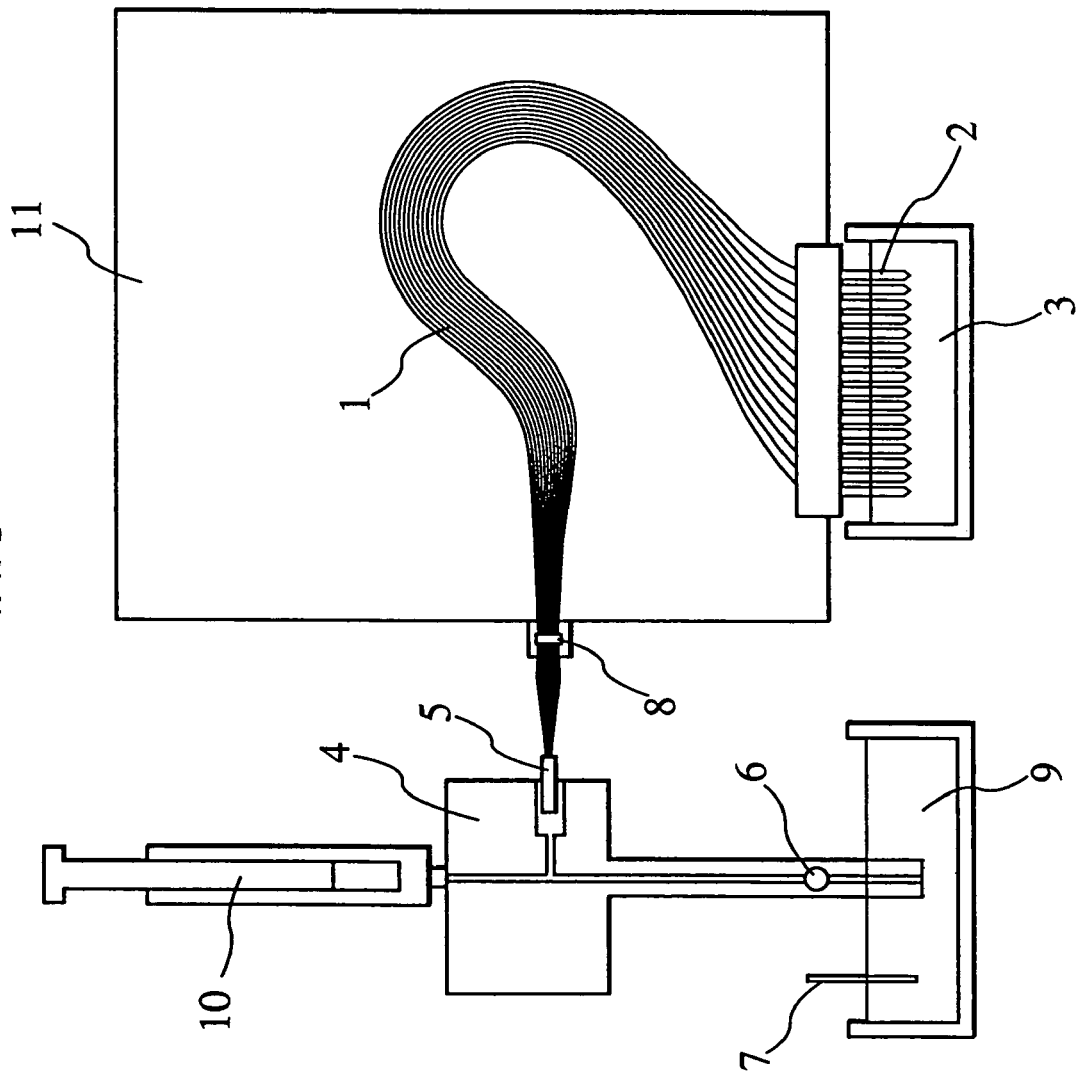
FIG. 1 is a schematic view of an example of an electrophoresis device according to the present invention.

FIG. 1 is a schematic view of an electrophoresis device according to the present invention. At one end of a capillary array 1, an electrode (sample inlet end) 2 is formed so that it can apply a negative voltage. The voltage is applied after soaking the negative electrode 2 into a solution containing the sample DNA (not shown) in the case of injecting the sample DNA, and after soaking the negative electrode 2 into a buffer solution 3 in the case of conducting electrophoresis of the injected sample DNA. Formed on the other end of the capillary array 1 is a connecting portion 5 for connecting the capillary array 1 with a gel block 4 from which an electrophoresis medium gel is injected into a capillary. In order to fill the capillary with the electrophoresis medium gel, a valve 6 is closed and a syringe 10 is pressed so that the gel retained in the syringe 10 is injected into the capillary 1. In the case of conducting the electrophoresis, the valve 6 is opened, and a voltage is applied between the negative electrode 2 soaked into the buffer 3 and an earth electrode 7 soaked into a buffer 9. The DNA in the sample is separated into fragments according to molecular weights and so forth as it migrates to the earth electrode 7 from the negative electrode 2 in the capillary 1 to generate a DNA band in the capillary 1. A fluorescent dye molecule is bonded to each of the synthetic DNA fragments. Laser beam irradiated on an irradiation area 8 of the capillary array 1 causes the fluorescent dye molecules to emit light, so that emission spectra of the emissions are measured by fluorescence measuring means to determine a base sequence and a base length of the DNA. Temperature in the capillary 1 is maintained constant by a gas-circulation-type oven 11. It should be noted that, in this specification, a section in the capillary array electrophoresis device shown in FIG. 1, which relates to the fluorescence measurement, is sometimes referred to as a capillary array photodetector.

Referring to FIG. 2A and FIG. 2B, an example of the capillary array of the present invention will be described. Each of these drawings shows a structure of a glass substrate and a state wherein the capillary array is fixed on the glass substrate. FIG. 2A is a front view of a part of the capillary array fixed on the planar grass substrate, and FIG. 2B is a sectional view taken along the line A—A of FIG. 2A.

In the examples shown in the drawings, the capillary array is formed of sixteen capillaries 21 that are aligned on a capillary holding surface 75 as a planar surface of a flat grass substrate 20 and fixed thereon with an adhesive or the like. Each of the capillaries 21 is a silica tube with a polymer coating. A portion to be irradiated with a laser beam, which will be described later in this specification, is not formed with the polymer coating with the silica tube being exposed. Inner and outer diameters of the silica tube respectively are 50 μm and 323 μm, and an outer diameter of the capillary including the polymer coating is 363 μm. Pitch of the capillaries is 363 μm, which is equal to the capillary outer diameter, and a width of the array is 5.8 mm (363 μm×16).

The planar glass substrate 20, on which the capillaries 21 are aligned is formed with a perforation 72 at an area in the rear of the capillaries when the capillary array is viewed from a fluorescence detector, which will be described later in this specification. On the surface of the glass substrate 20 excluding the perforation 72, grooves 73 are formed along light paths for laser beams in order to prevent the laser beams from contacting the surface of the substrate.

FIG. 3A and FIG. 3B are block diagrams respectively showing a detection unit of the capillary array and a guiding path for laser beam; FIG. 3A is a schematic front view of an example of an optical system of a capillary array photodetector according to the present invention, and FIG. 3B is a top view showing the detection unit of the capillary array. A shutter, a filter and so forth are provided in an optical system actually used, although they are not shown in the drawings for brevity. In FIG. 3A, reference numeral 22 denotes a first capillary, and reference numeral 23 denotes a sixteenth capillary.

A laser beam emitted by a laser 29 is split into halves by a beam splitter 30, and two laser beams 25 and 26 thus obtained are reflected from a reflection mirror 31 to enter the capillary array respectively from two directions that are opposite to each other. The laser beams 25 and 26 respectively are condensed by laser condenser lenses 27 and 28 (f=50 mm), and then irradiated on the fluorescence detection portion (laser irradiation portion) 24 of the capillary array from both side surfaces thereof. Each of distances between the laser condenser lens 27 and the first capillary 22 and between the laser condenser lens 28 and the sixteenth capillary 23 is 50 mm.

Figure 4:
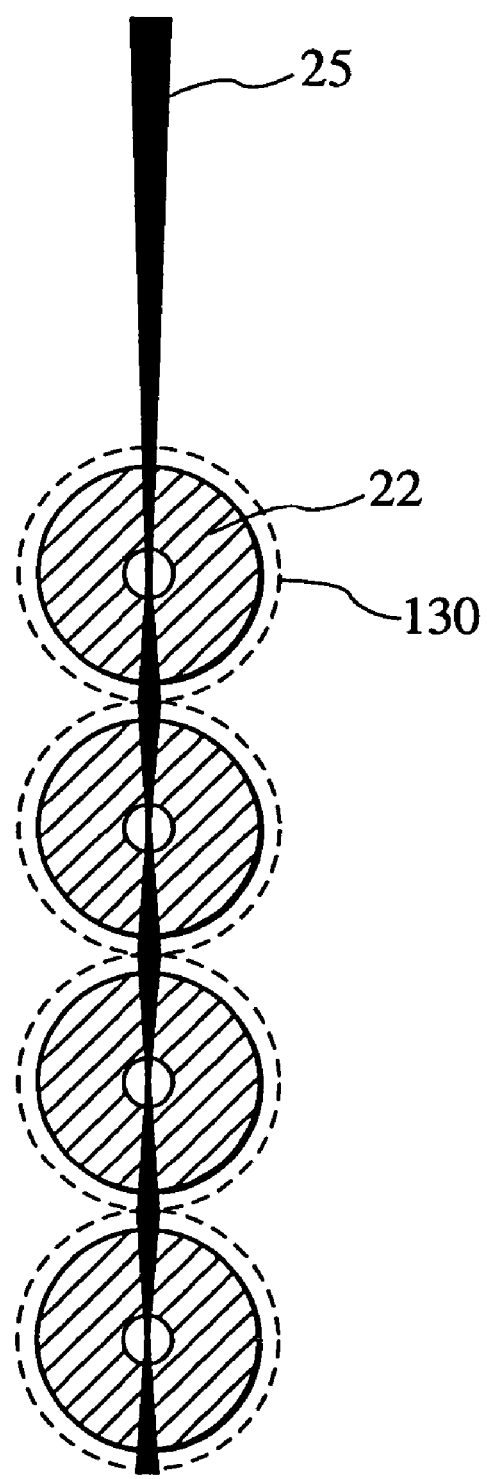
FIG. 4 is a schematic diagram showing a laser beam path in a cross-section of the capillary array.

As shown in FIG. 4, the laser beam 25 guided into the first capillary 22 propagates across the sixteen capillaries one by one in such a manner that the laser beam 25 passes through the gel in each of the capillaries while being refracted at an interface between an ambient atmosphere and each of the silica tubes and at an interface between each of the silica tubes and the gel inside the silica tube and repeating focusing and divergence, thereby exciting the fluorescent dye in the capillaries. Reference numeral 130 in the drawing denotes a polyimide coating peeled off for the laser irradiation portion 24.

Figure 5:
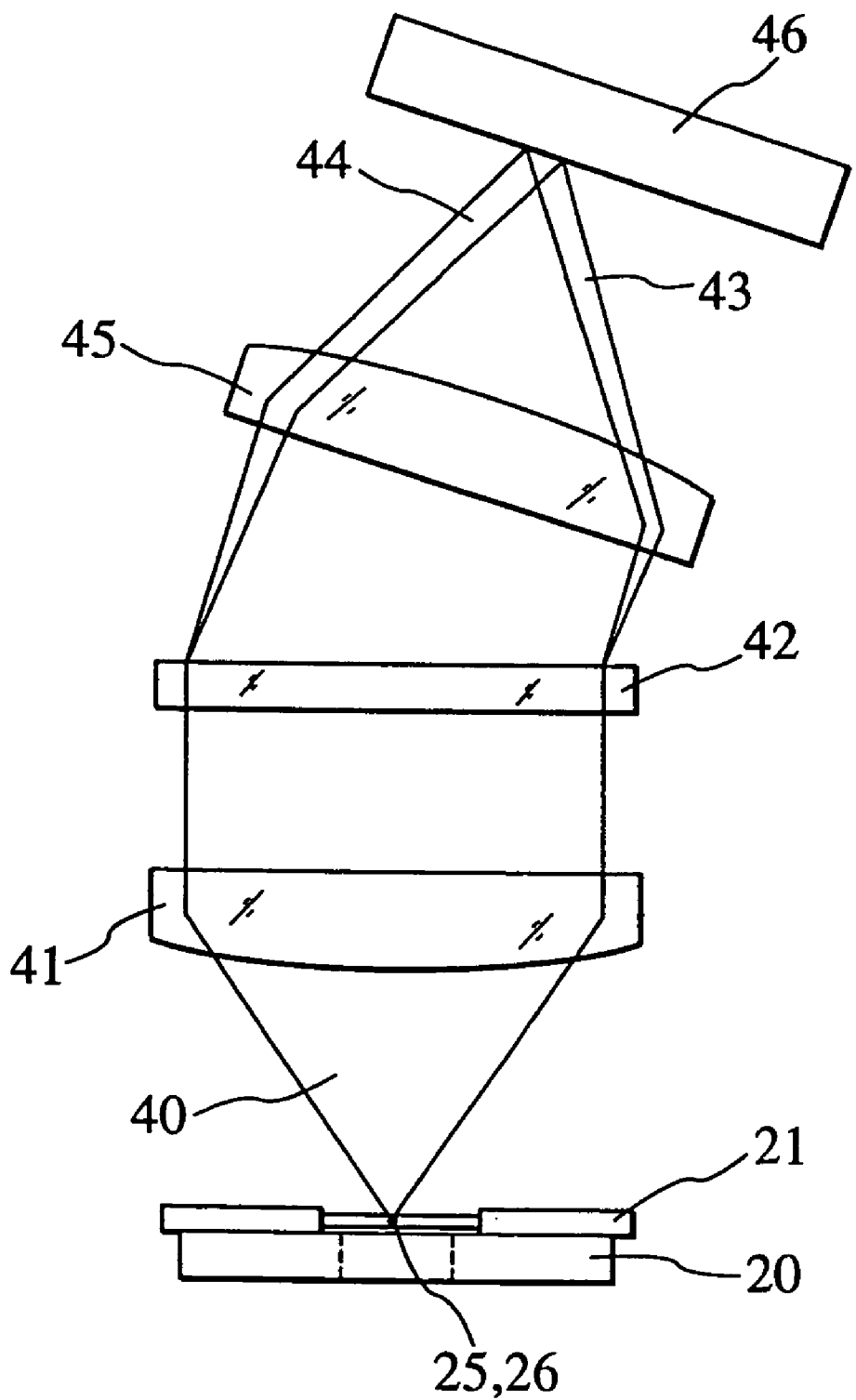
FIG. 5 is a top view showing an example of a fluorescence detection system.

FIG. 5 is a top view showing schematically a fluorescence detection system. An optical axis of each of the laser beams 25 and 26 is perpendicular to the drawing sheet. Emissions 40 in one of the capillaries 21 are modified to be substantially parallel light by using an emission condenser lens 41 (f=1.4) to be guided into a transmission grating 42. The transmission grating 42 splits the light to generate pieces of light 43 and 44 that are focused on a two-dimensional CCD 46 via a focusing lens 45. Wavelength dispersion direction according to the transmission grading 42 is perpendicular to the laser optical axis. Therefore, one of the two orthogonal axes on the two-dimensional CCD 46 represents space coordinates of the direction of alignment of the sixteen capillaries, and the other represents emission spectra from the capillaries. From the emission spectra, fluorescence labeled DNA is detected and identified.

Figure 6:
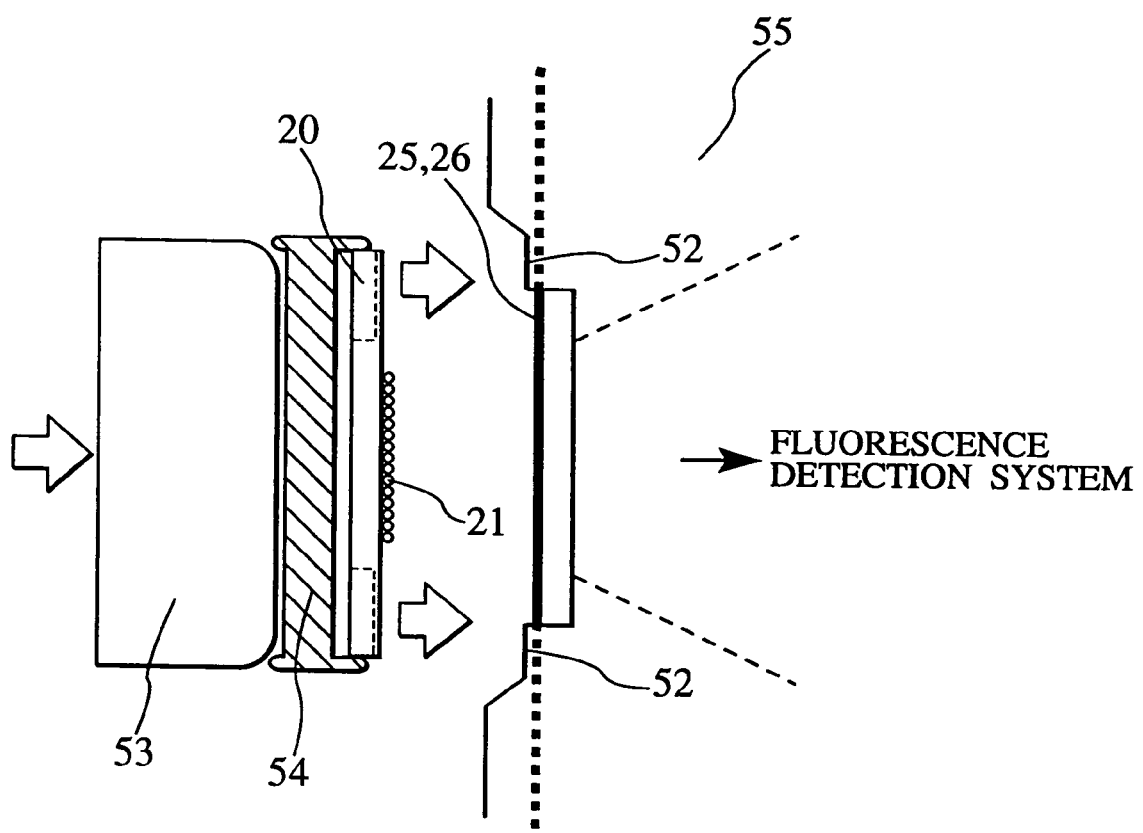
FIG. 6 is a view showing an example of a method of mounting the capillary array to the capillary array photodetector.

FIG. 6 shows a method of mounting the capillary array to the capillary array photodetector. In the multi-focus irradiation system, it is necessary to mount a reproducible capillary array since a relative alignment precision between the laser optical axis of the capillary array photodetector and the capillary array is important. Therefore, as shown in FIG. 6, a part of the planar glass substrate 20 on which the capillaries 21 are aligned is brought into contact with a mounting reference surface 52 of a capillary array photodetector 55, so that the capillary array is pressed against the photodetector 55 by array fixing means 53. In the example shown in FIG. 6, a capillary array holder 54 is so mounted on the planar glass substrate 20 that handling of the capillary array can be facilitated, and the array fixing means 53 presses the planar glass substrate 20 against the mounting reference surface 52 of the capillary array photodetector 55 via the capillary array holder 54.

The laser beams 25 and 26 propagate across the gel portions of the sixteen capillaries one by one to excite the fluorescence dyes bonded to the DNA migrating in the gel as described with reference to FIGS. 3A to 5 in the state where a part of a capillary fixing side plane of the planar glass substrate 20, on which the capillary array is fixed, is contacted with and fixed to the mounting reference surface 52 on the capillary array photodetector 55. The emissions from the fluorescent dyes are detected by the fluorescence detection system in the capillary array photodetector 55 as described with reference to FIG. 5.

Figure 7:
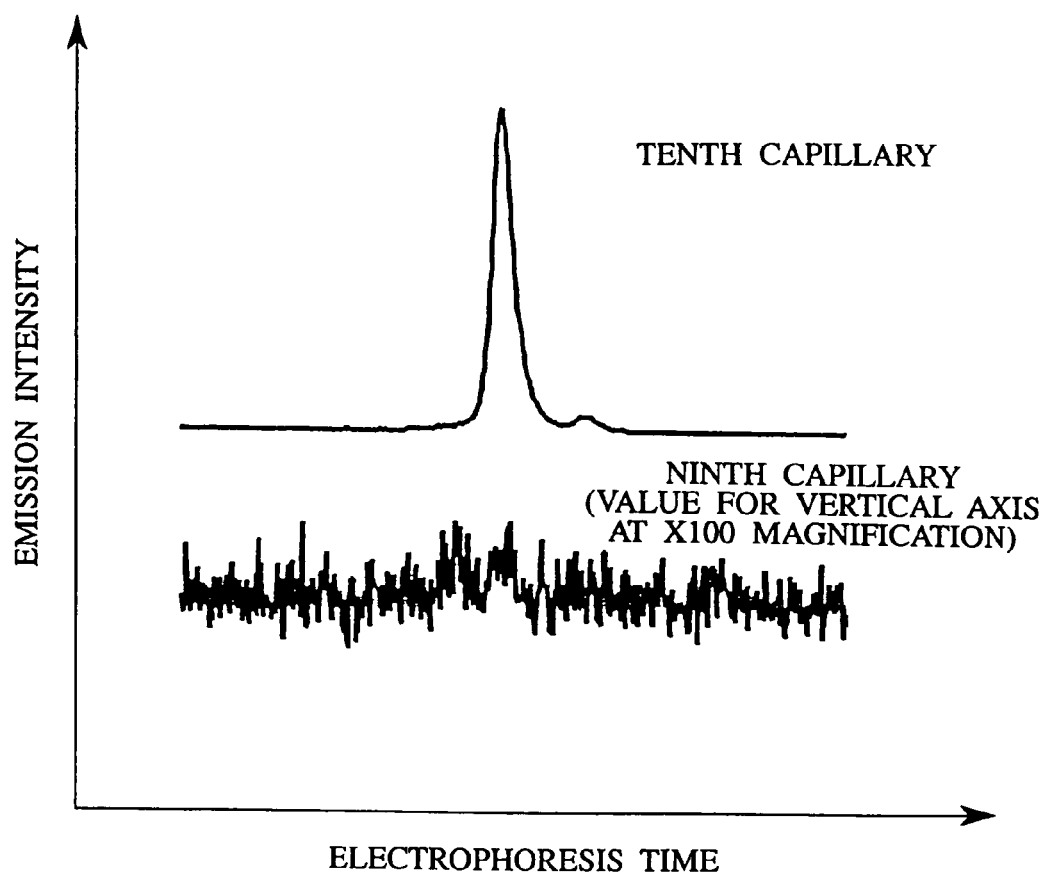
FIG. 7 is a graph showing measurement results of crosstalk in the capillary array according to the present invention.

FIG. 7 is a graph showing measurement results obtained by injecting a sample containing DNAs of a single base length into the tenth capillary of the capillary array of the present invention. In FIG. 7, fluorescent signals detected from a position of a ninth capillary that is adjacent to the tenth capillary are plotted in addition to fluorescent signals detected from a position of the tenth capillary. It should be noted that values for the vertical axis of the fluorescent signals detected from the ninth capillary position are plotted as being magnified 100 times. Since the DNA sample was injected only into the tenth capillary, the signals observed at the ninth capillary position are crosstalk. The crosstalk observed under these electrophoresis conditions was 0.1%.

In turn, FIG. 8A, FIG. 8B and FIG. 8C each shows a state wherein a capillary array is mounted on a glass substrate according to a conventional system; FIG. 8A is a front view, FIG. 8B is a side elevation taken along the line A—A of FIG. 8A, and FIG. 8C is a sectional view viewed from a direction parallel to a light path of laser beam.

Sixteen capillaries 71 are aligned on a planar glass substrate 70. On a capillary holding surface of the planar glass substrate, a groove 62 is formed along a light path for laser beams in order to avoid contact of laser beams with the planar glass substrate 70. Due to the grooving, a glass surface 63 corresponding to a part of the groove 62 is in the state of a frosted glass.

Figure 9:
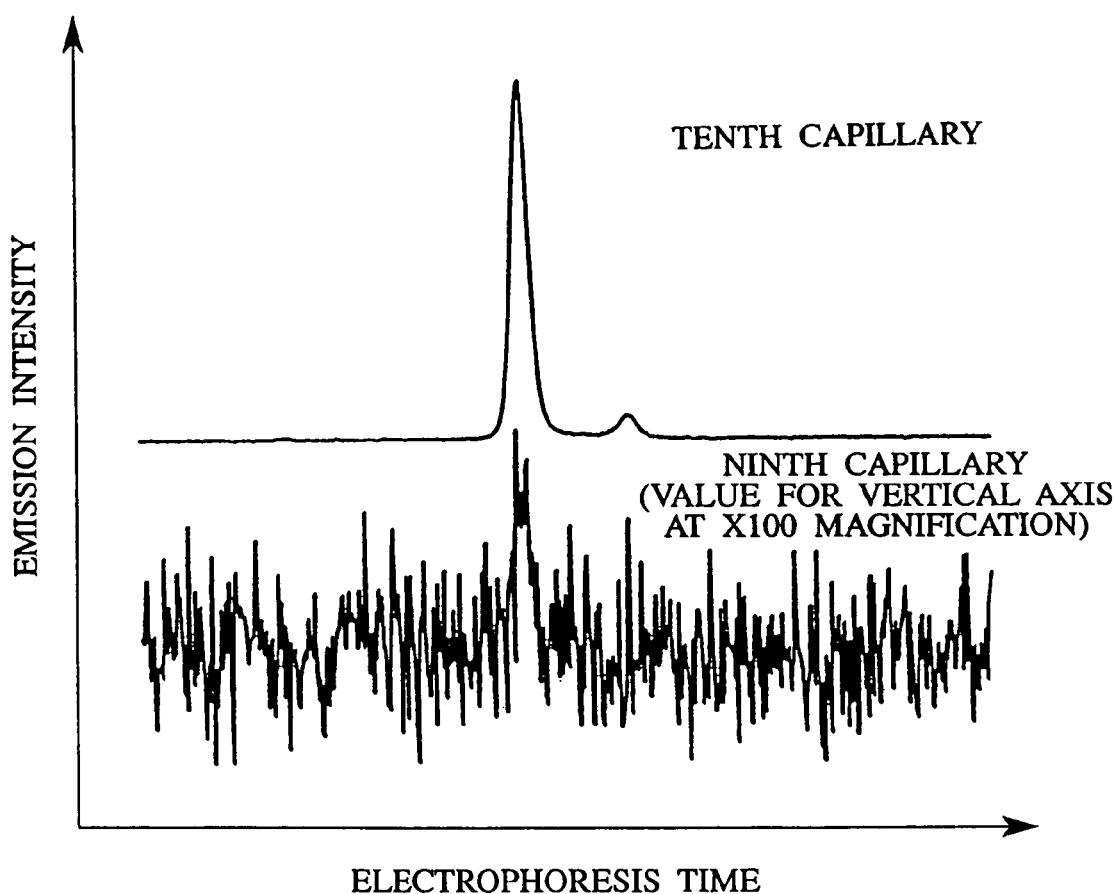
FIG. 9 is a graph showing measurement results of crosstalk in a conventional capillary array.

FIG. 9 is a graph showing measurement results when a sample containing DNAs of a single base length is injected into the tenth capillary in the conventional capillary array. In FIG. 9, fluorescent signals detected from a position of a ninth capillary that is adjacent to the tenth capillary are plotted in addition to fluorescent signals detected from a position of the tenth capillary. It should be noted that values for the vertical axis of the fluorescent signals detected from the ninth capillary position are plotted as being magnified 100 times. Since the DNA sample was injected only into the tenth capillary, the fluorescent signals are supposed to be detected only from the tenth capillary position, but not from the ninth capillary position. However, as shown in FIG. 9, there occurred crosstalk in the signals detected from the tenth capillary position, which were also observed in the ninth capillary position. In this case an amount of the crosstalk was 0.4%.

Thus, as it is apparent from the comparison with the conventional system, according to the present embodiment, the crosstalk was reduced owing to the perforation 72 formed in the planar glass substrate in place of the conventional groove 62.

Second Embodiment

Figure 10:
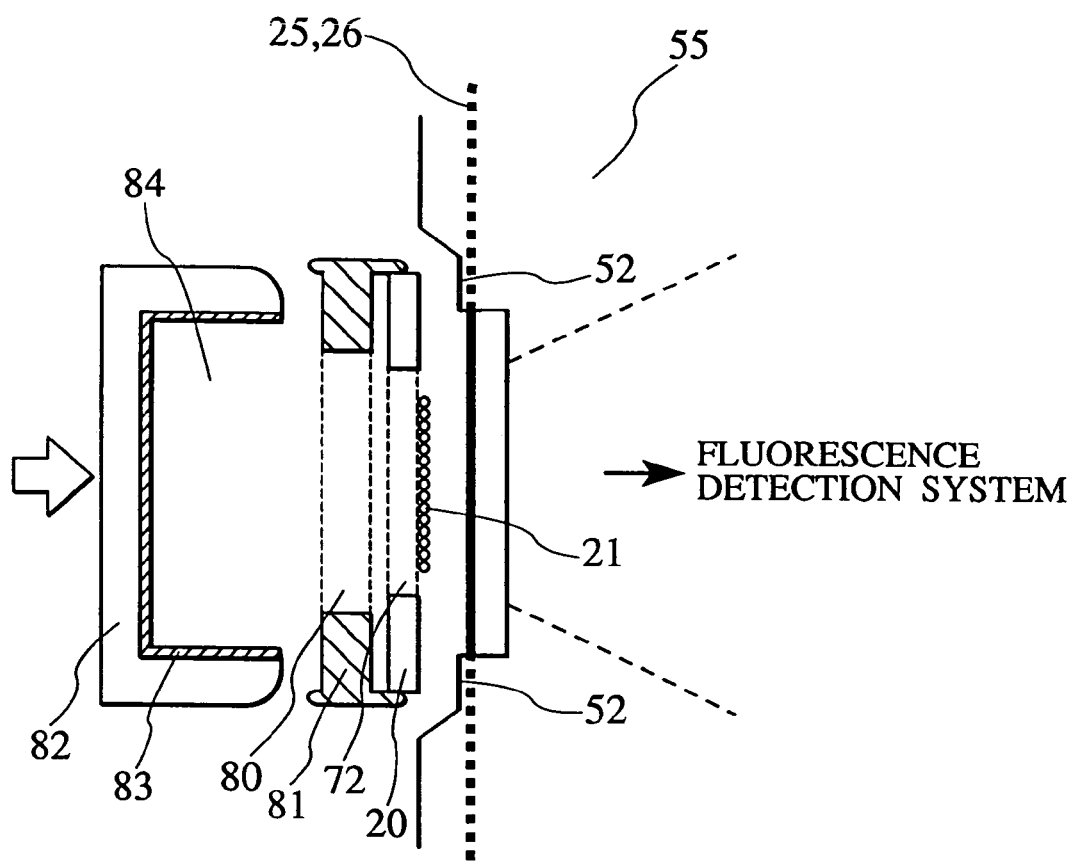
FIG. 10 is a sectional view of another example of a capillary array photodetector and a vicinity of an area on which laser beam is irradiated according to the present invention.
Figure 11:
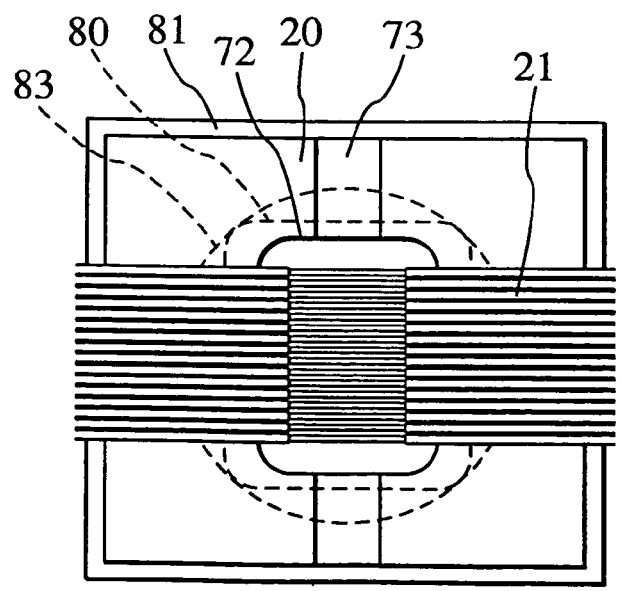
FIG. 11 is a front view of FIG. 10.

A second embodiment of the present invention will be described with reference to FIGS. 10 and 11. FIG. 10, which corresponds to FIG. 6, is a sectional view of another example of a capillary array photodetector and a vicinity of an area on which laser beam is irradiated. FIG. 11 is a front view of FIG. 10.

In the present embodiment, as shown in FIGS. 10 and 11, a capillary array holder 81 placed at the rear of the planar glass substrate 20 is formed with a perforation 80, in addition to th perforation 72 formed on the planar glass substrate when the capillary array is viewed from the fluorescence detector provided in the capillary array photodetector. Further, a cavity 84 is formed on a side facing to the capillary array of an array fixing means 82 for fixing the capillary array, so that emissions from the capillaries 71 enter the cavity 84. A black coating that is remarkably low in reflectance is applied on an inner wall 83 of the cavity 84 provided on the array fixing means 82. Other configuration are the same as those of the first embodiment.

According to the present embodiment, crosstalk detected with respect to a capillary adjacent to a capillary on which the laser beam was irradiated was 0.05% and, thus, it was confirmed that the capillary array of the present invention reduces the crosstalk more effectively than that achieved by the conventional capillary array.

Third Embodiment

A third embodiment will be described with reference to FIGS. 12A and 12B. FIG. 12A is a front view of a part of a capillary array fixed on a planar glass substrate, and FIG. 12B is a sectional view taken along the line A—A of FIG. 12A.

Conventionally, the groove 62 has been formed along the light path of laser beams on the planar glass substrate 70 in order to avoid contact of the laser beam with the planar glass substrate 70 as described with reference to FIG. 8. The glass surface 63 corresponding to a part of the groove has been in the state of a frosted glass due to the grooving. In turn, in the present embodiment, grooves 90 for avoiding contact of the laser beams with the planar glass substrate 91 are respectively formed on opposite ends of a planar glass substrate 91, but not in an area in which capillaries 92 are aligned.

There will be explained reasons for the sufficient avoidance of contact of the laser beams with the planar glass substrate 91 that is achieved by the grooves formed at opposite ends of the planar glass substrate according to the present embodiment. As described with reference to FIGS. 3A and 3B, since the laser beams are condensed by the lenses to be irradiated on the capillary array, a diameter of each of the beams is increased as they approach to the ends of the planar glass substrate 91, while it is reduced as they approach to the capillaries 92. Since each of the beam diameters is sufficiently smaller than a capillary diameter in the vicinity of the capillaries 91 and each of the laser beams enters each of the capillaries from an approximately center position (a portion filled with the gel), the laser beams do not contact with the planar glass substrate 91 though there is no groove in the vicinity of the capillaries. However, at the ends of the planar glass substrate 91, the laser beams possibly contact with the planar glass substrate 91 if the grooves 90 are not formed.

According to the present embodiment, crosstalk detected with respect to a capillary adjacent to a capillary on which the laser beam was irradiated was 0.25% and, thus, it was confirmed that the capillary array of the present embodiment reduces the crosstalk as compared with the conventional one.

Fourth Embodiment

A fourth embodiment will be described with reference to FIGS. 13A and 13B. FIG. 13A is a front view of a part of the capillary array fixed on a planar glass substrate, and FIG. 13B is a sectional view taken along the line A—A of FIG. 13A.

A planar glass substrate 101 for fixing a capillary array of the present embodiment is not provided with a groove for avoiding contact of laser beams with the planar glass substrate. By downsizing the planar glass substrate 101, or by irradiating the planar glass substrate 101 with each of the laser beams at a certain angle as indicated by a broken line 100 in FIG. 10B with respect to the planar glass substrate 101, it is possible to avoid contact of the laser beams with the glass pate 101.

As described below, it is possible to irradiate all the capillaries of the capillary array with a laser beam by irradiating the planar glass substrate with the laser beam at a certain angle with respect, and the laser beam is not necessarily irradiated in parallel with respect to the planar glass substrate. Since each of the capillaries functions as a rod lens, it is possible to control a laser beam outgoing angle, at which the laser beam outgoes to an adjacent capillary from a capillary (end capillary) on which the laser beam is firstly irradiated, depending on a laser beam irradiation position of the end capillary. Therefore, by properly setting the laser beam irradiation position of the first capillary, it is possible to propagate the laser beam to all the capillaries aligned in parallel to the planar glass substrate even if the laser beam is irradiated on the capillary at a angle with respect to the capillary array.

According to the present embodiment, crosstalk detected with respect a capillary adjacent to a capillary on which the laser beam was irradiated was 0.25% and, thus, it was confirmed that the capillary array of the present embodiment reduces the crosstalk as compared with the conventional one.

Fifth Embodiment

In the same configuration as that shown in FIG. 13, a monolayer anti-reflection coating of magnesium fluoride ($MgF_2$) is formed on a glass substrate surface on which capillary array is provided. Crosstalk detected in this embodiment was 0.2% and, thus, it was confirmed that the capillary array of the present embodiment reduces the crosstalk as compared with the conventional one.

Sixth Embodiment

Figure 14A:
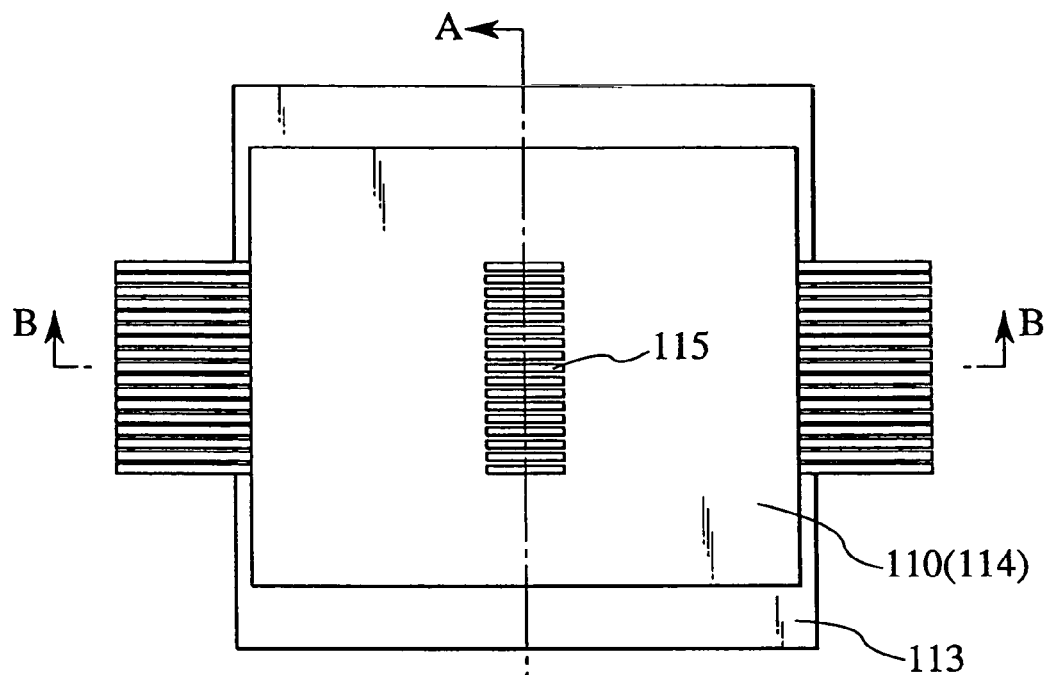
FIG. 14A, FIG. 14B, FIG. 14C and FIG. 14D each shows a capillary array with a mask.
Figure 14B:
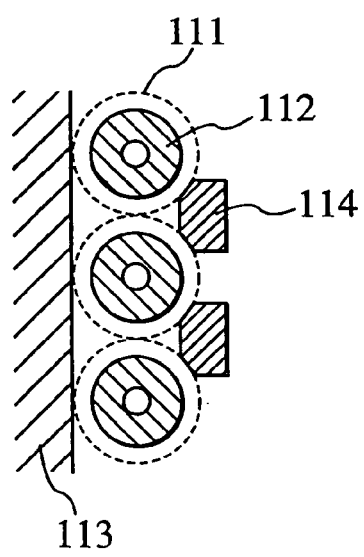
Figure 14C:
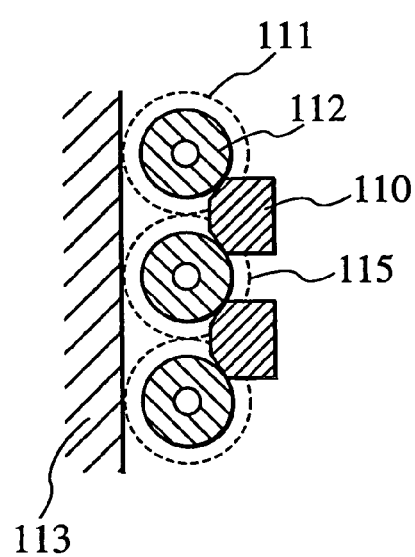
Figure 14D:
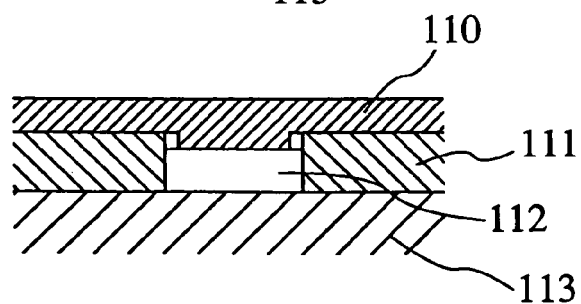

A capillary array with a mask according to the present embodiment will be described with reference to FIGS. 14A to 14D. FIG. 14A is a front view of the capillary array with mask, FIG. 14B is a sectional view taken along the line A—A of a conventional capillary array with mask, FIG. 14C is a sectional view taken along the line A—A of an example of a capillary array according to the present invention, and FIG. 14D is a sectional view taken along the line B—B of the capillary array according to the present invention.

In the capillary array of the present embodiment, scattered light is shielded by attaching a mask 110 to the capillary array fixed on a planar glass substrate 113. The attachment of a mask to a capillary array has been realized in the art. However, such conventional mask as denoted by reference numeral 114 in FIG. 14B contacts with a polyimide coating 111 of the capillary, but not with a glass portion 112 of a capillary a coating of which is not applied. Therefore, there is a gap between the glass 112 of the capillary and the mask 114, through which the scattered light passes from an capillary adjacent to a target capillary on which the laser beam is irradiated to be detected as signals from the target capillary, thereby causing crosstalk. Hence, in the present embodiment, as shown in the sectional view of FIG. 14C and the sectional view of FIG. 14D, a structure of the mask 114 which does not cause a gap between the glass portion 112 of each of the capillaries and the mask 110 is employed. That is to say, a thickness of a portion of the mask 110 in an area covering the irradiation portion provided with a window 115 for each capillary, is increased so that the mask contacts with the glass portion 112 exposed by removing the coating on the capillary. An area between the mask 110 and the coating-removed portion of the capillary may be filled with a light shielding material.

According to the capillary array employing the mask structure of the present embodiment, crosstalk detected with respect to the capillary adjacent to the target capillary was 0.3% and, thus, it was confirmed that the capillary array of the present embodiment reduces the crosstalk as compared with the conventional one.

Seventh Embodiment

Figure 15A:
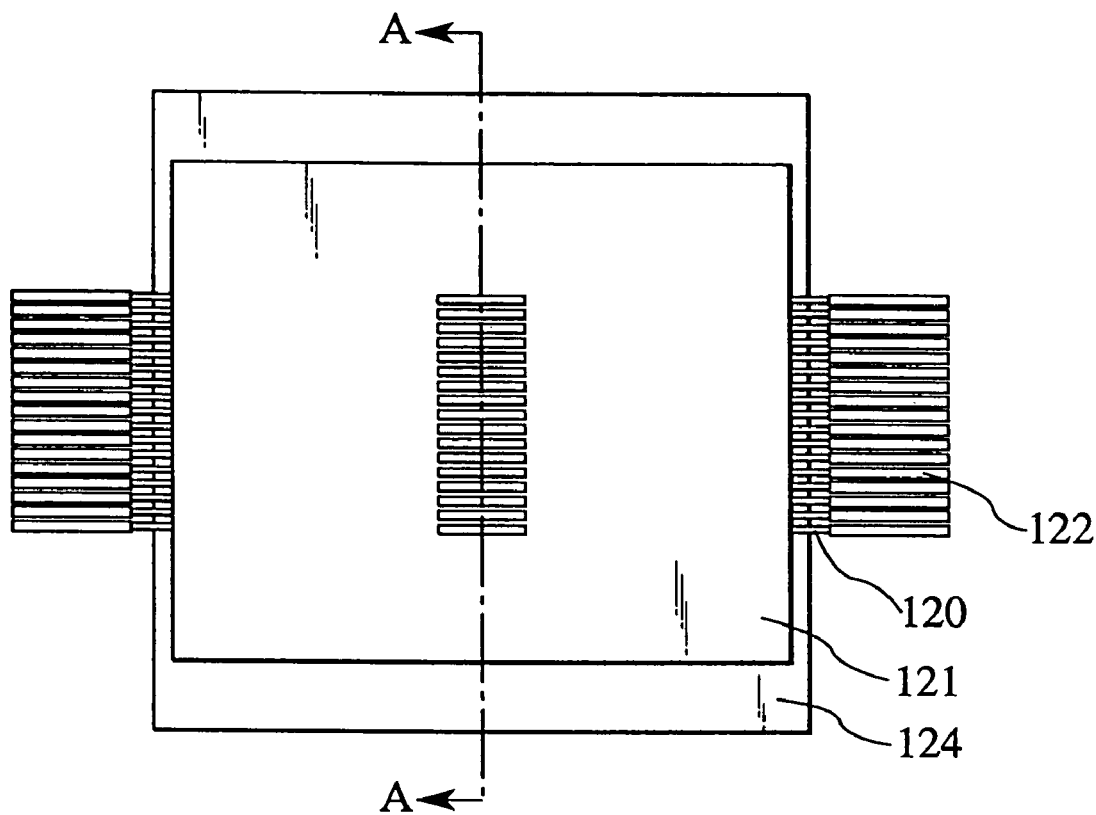
FIG. 15A and FIG. 15B each shows another example of a capillary array with a mask according to the present invention.
Figure 15B:
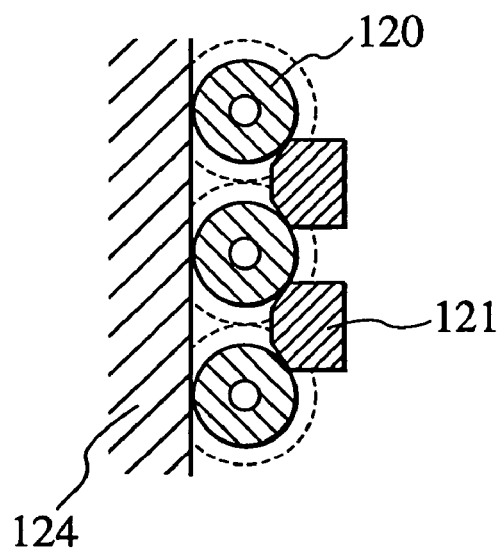

Seventh embodiment will be described with reference to FIGS. 15A and 15B. FIG. 15A is a front view thereof, and FIG. 15B is a sectional view taken along the line A—A of FIG. 15A.

In the capillary array of the present embodiment, scattered light is shielded by attaching a mask 121 to the capillary array fixed on a planar glass substrate 124. In the present embodiment, a width of a coating-removed portion 120 of each of the capillaries 122 is made wider than a width of the mask 121, so that the mask 121 does not contact directly with the coating-removed portion 120 of each of the capillaries 122. In the present embodiment, too, no gap exists between each of the capillaries and the mask.

According to the capillary array employing the mask configuration of the present embodiment, crosstalk detected with respect to a capillary adjacent to a capillary on which the laser beam was irradiated was 0.3% and, thus, it was confirmed that the capillary array of the present embodiment reduces the crosstalk as compared with the conventional one.

What is claimed is:

1. A capillary array comprising a substrate having a planar capillary holding surface and a plurality of capillaries aligned on the capillary holding surface of the substrate, wherein a laser beam irradiated on a capillary at one end or capillaries at both ends of the plurality of capillaries in a substantially parallel direction with respect to the capillary holding surface propagates to all the plurality of capillaries one by one to travel through the capillaries, and emissions from each of the capillaries are detected in a substantially perpendicular direction with respect to the capillary holding surface,
    wherein the substrate is provided with a through hole extending from the capillary holding surface to a back side of the substrate in an area opposing to portions of the plurality of capillaries each of which receives the laser beam irradiation, and wherein the substrate aligning the capillaries exists at the back of the capillaries when the capillary array is viewed from a fluorescence detector.

2. A capillary array photodetector comprising a reference surface which contacts with a capillary holding surface of a capillary array holding substrate that holds a capillary array, fixing means for fixing the capillary array holding substrate brought into contact with the reference surface by pressing the capillary array holding substrate from the rear surface thereof, a laser light source, an irradiation optical system for setting a part of a light path extending from the light source to be substantially parallel to the capillary holding surface of the capillary array holding substrate contacting with the reference surface, and a photodetector system for detecting emissions,
    the capillary array photodetector detecting emissions from each of the capillaries, which emissions being caused by laser beam that is irradiated from the irradiation optical system on a capillary at one end or capillaries at both ends of the plurality of capillaries aligned on the capillary holding surface of the capillary array holding substrate fixed on the reference surface with being brought into contact therewith and that propagates to all the plurality of capillaries one by one to travel through the capillaries,
    wherein the capillary array holding substrate is provided with a through hole extending from the capillary holding surface to a back side of the capillary array holding substrate in an area opposing to portions of the plurality of capillaries each of which receives the laser beam irradiation,
    and wherein the fixing means is provided with a recessed portion opening on a side of the reference surface, and wherein the substrate aligning the capillaries exists at the back of the capillaries when the capillary array is viewed from a fluorescence detector.

3. The capillary array photodetector according to claim 2, wherein a surface of the recessed portion of the fixing means is subjected to a light-scattering prevention treatment or a light-reflection prevention treatment.

4. The capillary array according to claim 1, wherein the substrate is a flat glass substrate.

5. The capillary array according to claim 1, wherein the substrate has a groove that is formed along the laser beam.

6. The capillary array according to claim 1, wherein the substrate couples with a capillary array holder.

7. The capillary array according to claim 6, wherein the substrate is capable of mounting a capillary array photodetector via the capillary array holder.

8. The capillary array according to claim 6, wherein the capillary array holder has a perforation.

9. The capillary array photodetector according to claim 2 further comprising a transmission grating.

10. The capillary array photodetector according to claim 2 further comprising a two-dimensional CCD.

11. The capillary array photodetector according to claim 2, wherein a surface of the recessed portion of the fixing means is treated with a non-fluorescent black coating.

12. The capillary array photodetector according to claim 2, wherein a surface of the recessed portion of the fixing means is treated with a blackening treatment of a copper surface.

13. The capillary array photodetector according to claim 2, wherein a surface of the recessed portion of the fixing means comprises a light absorption material.

14. An electrophoresis apparatus comprising:
    a plurality of capillaries capable of being filled with an electrophoresis medium for separating fragments according to molecular weights thereof;
    an irradiation optical system for irradiating a laser beam, wherein the laser beam is propagated to the capillaries one-by-one to travel through the capillaries;
    a photodetector system for detecting emissions from each of the capillaries; and,
    a substrate for aligning the capillaries, wherein the substrate has a perforation in an area opposite to portions of the capillaries each of which receives the laser beam, and wherein the substrate aligning the capillaries exists at the back of the capillaries when the capillaries are viewed from a fluorescence detector.

15. The electrophoresis apparatus according to claim 14, wherein an irradiation optical system irradiates two laser beams, and wherein two laser beams enter the plurality of capillaries respectively from two directions that are opposite to each other.

16. The electrophoresis apparatus according to claim 14 further comprising an array fixing means for holding the substrate.

17. The electrophoresis apparatus according to claim 14 further comprising:
a capillary array holder coupled with the substrate; and
an array fixing means for holding the substrate via the capillary array holder.

18. The electrophoresis apparatus according to claim 14 further comprising a capillary array holder coupled with the substrate, wherein the capillary array holder has a perforation.

19. The electrophoresis apparatus according to claim 14 further comprising an array fixing means for holding the substrate, wherein the array fixing means has a cavity, and wherein the emissions from the capillaries are capable of entering the cavity.

20. The electrophoresis apparatus according to claim 19, wherein an inner wall of the cavity surface prevents light-scattering or light reflecting.

21. An electrophoresis apparatus comprising:
a plurality of capillaries capable of being filled with an electrophoresis medium for separating fragments according to molecular weights thereof;
an irradiation optical system for irradiating a laser beam, wherein the laser beam is propagated to the capillaries one-by-one to travel through the capillaries;
a photodetector system for detecting emissions from each of the capillaries;
a substrate for aligning the capillaries, wherein the substrate has a perforation in an area opposite to portions of the capillaries each of which receives the laser beam; and wherein an irradiation optical system irradiates two laser beams, and wherein two laser beams enter the plurality of capillaries respectively from two directions that are opposite to each other.

22. The electrophoresis apparatus according to claim 21 further comprising an array fixing means for holding the substrate.

23. The electrophoresis apparatus according to claim 21 further comprising:
a capillary array holder coupled with the substrate; and
an array fixing means for holding the substrate via the capillary array holder.

24. The electrophoresis apparatus according to claim 21 further comprising a capillary array holder coupled with the substrate, wherein the capillary array holder has a perforation.

25. An electrophoresis apparatus comprising:
a plurality of capillaries capable of being filled with an electrophoresis medium for separating fragments according to molecular weights thereof;
an irradiation optical system for irradiating a laser beam, wherein the laser beam is propagated to the capillaries one-by-one to travel through the capillaries;
a photodetector system for detecting emissions from each of the capillaries;
a substrate for aligning the capillaries, wherein the substrate has a perforation in an area opposite to portions of the capillaries each of which receives the laser beam; and
an array fixing means for holding the substrate, wherein the array fixing means has a cavity, and wherein the emissions from the capillaries are capable of entering the cavity.

26. The electrophoresis apparatus according to claim 25, wherein an inner wall of the cavity surface prevents light-scattering or light reflecting.

* * * * *